United States Patent [19]

Stapley

[11] Patent Number: 4,521,408

[45] Date of Patent: Jun. 4, 1985

[54] ANTIBIOTICS-859A AND PRODUCTION THEREOF

[75] Inventor: Edward O. Stapley, Metuchen, N.J.

[73] Assignee: Merck & Co., Inc., Rahway, N.J.

[21] Appl. No.: 368,339

[22] Filed: Apr. 14, 1982

[51] Int. Cl.³ .......................... A61K 35/00; C12P 1/06
[52] U.S. Cl. ..................................... 424/115; 435/169
[58] Field of Search ......................... 424/115; 435/169

[56] References Cited

U.S. PATENT DOCUMENTS 4,180,564 12/1979 Godfrey et al. .................... 424/115

*Primary Examiner*—Jerome D. Goldberg
*Attorney, Agent, or Firm*—Ernest V. Linek; Raymond M. Speer; Hesna J. Pfeiffer

[57] ABSTRACT

The mixture, Antibiotics-859A and the production thereof is described. The Antibiotics-859A are produced by the controlled aerobic cultivation of *Streptomyces griseoruber*, ATCC 39068 in an aqueous nutrient medium. The Antibiotics-859A exhibit activity both in vitro and in vivo against gram negative and gram positive organisms including the genera: Diplococcus, Staphylococcus, Streptococcus, Pseudomonas and Salmonella.

8 Claims, 2 Drawing Figures

INFRA RED SPECTRUM OF THE ANTIBIOTICS 859A

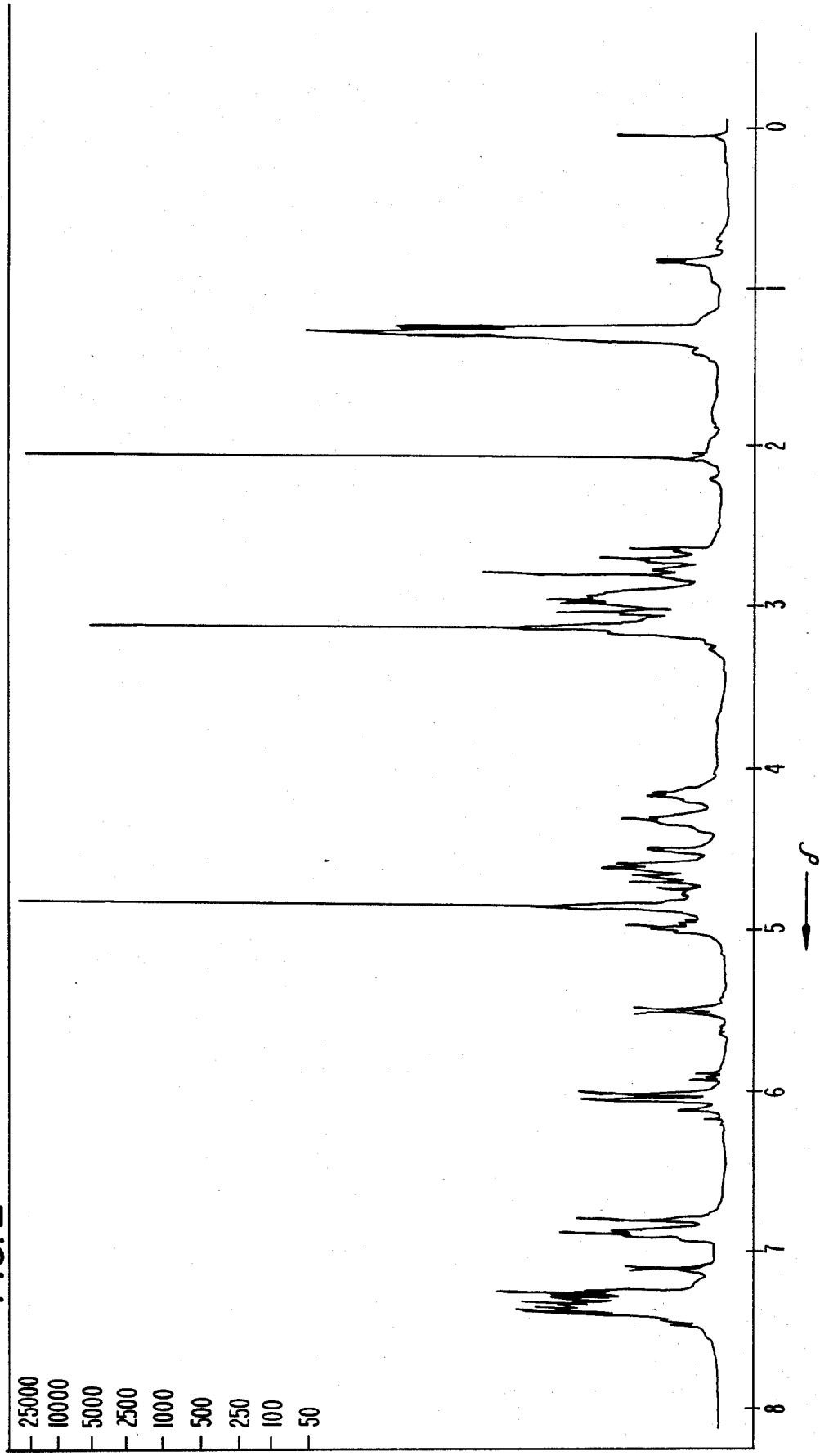
FIG. 2  NUCLEAR MAGNETIC RESONANCE (NMR) SPECTRUM OF 859A

ANTIBIOTICS-859A AND PRODUCTION THEREOF

BACKGROUND OF THE INVENTION

The present invention is directed toward the Antibiotics-859A and the production thereof. The Antibiotics-859A are different from other know Antibiotic. The only antibiotic mixture that is similar in spectrum of activity and composition is A-38533 which is fully described in *Godfrey et al.*, U.S. Pat. No. 4,180,564.

SUMMARY OF THE INVENTION

In particular, the present invention relates to the novel compounds, Antibiotics-859A, having antibacterial activity against gram-positive organisms such as: *Diplococcus pneumoniae, Staphylococcus aureus,* and *Streptococcus pyogenes,* and the gram-negative organisms; *Pseudomonas aeruginosa* and *Salmonella schottmuelleri.* There is no activity exhibited against the gram-negative organism *Proteus vulgaris.* The present invention is also directed to a method for producing the Antibiotics-859A, characterized by cultivating an Antibiotics-859A producing strain of *Streptomyces griseoruber,* ATCC 39068 in an aqueous nutrient medium under aerobic conditions and isolating the accumulated Antibiotics-859A from the cultured broth.

*Streptomyces griseoruber*, ATCC 39068 was isolated from a soil sample and represents a heretofore unknown microorganism. A biologically pure sample of this living organism has been deposited without restriction in, and made a part of, the American Type Culture Collection, Rockville, Md., from which it is available under accession No. ATCC 39068.

MORPHOLOGICAL AND CULTURAL CHARACTERISTICS OF *STREPTOMYCES GRISEORUBER* ATCC 39068

The cultural and morphological characteristics described herein have been compared to those descriptions of *Streptomyces* species in Bergey's *Manual of Determinative Bacteriology*, 8th Edition. The Williams and Wilkins Co.; E. B. Shirling and D. Gottlieb's "Cooperative Descriptions of Type Cultures of Streptomyces", *Int. J. Syst. Bact.*, 18, 69–189, 279–399 (1968); and S. A. Waksman, *The Actinomycetes*, Vol. 2, 1961, The Williams and Wilkins Company. The data shown below confirms that the culture ATCC No. 39608 has the major species-defining characteristics of *Streptomyces griseoruber.* Differences are minor and of a strain differentiating nature.

The cultural characteristics of *Streptomyces griseoruber* ATCC 39068 are as follows: (V=vetetative growth; A=aerial mycelium; SP=soluble pigment) Morphology: Sporophores form long, somewhat loosely coiled spirals branching off aerial mycelia and consisting of chains of more than 15 spores. Surface of spores as seen by electron microscope shows short spines.

Oatmeal agar (ISP Medium 3)
 V: Light reddish-brown
 A: Medium gray edged with light gray
 SP: None
Czapek Dox agar (sucrose nitrate agar)
 V: Dark red-brown
 A: None
 SP: Light reddish-brown
Egg albumin agar
 V: Reverse—dark reddish brown
 A: Medium gray
 SP: None
Glycerol asparagine agar (ISP Medium 5)
 V: Dark reddish-brown
 A: Moderate, edged with medium gray
 SP: None
Inorganic salts-starch agar (ISP Medium 4)
 V: Light reddish brown
 A: Scant, grayish
 SP: None
Yeast extract-malt extract agar (ISP Medium 2)
 V: Reverse—dark reddish brown
 A: Medium gray flecked with white
 SP: None
Peptone-iron-yeast extract agar
 V: Tan
 A: None
 SP: None
 Melanin: None
Nutrient tyrosine agar
 V: Tan
 A: None
 SP: Slight-browning of medium
 Decomposition of tyrosine: Tyrosine crystals decomposed
Tyrosine Agar (ISP Medium 7)
 V: Tan
 A: None
 SP: None
Carbon utilization
 Pridham-Gottlieb basal medium+1% carbon source;
  +=growth; ±=growth poor or questionable;
  −=no growth as compared to negative control (no carbon source)

| | |
|---|---|
| Glucose | + |
| Arabinose | + |
| Cellulose | − |
| Fructose | + |
| Inositol | + |
| Lactose | + |
| Maltose | + |
| Mannitol | + |
| Mannose | + |
| Raffinose | + |
| Rhamnose | + |
| Sucrose | + |
| Xylose | + |

Temperature range (Yeast extract-dextrose+salts agar)
 28° C.—Good vegetative and aerial growth with sporulation.
 37° C.—Moderate vegetative growth; moderate aerial growth
 50° C.—No growth

OXYGEN REQUIREMENT (STAB CULTURE IN YEAST EXTRACT-DEXTROSE +SALTS AGAR) AEROBIC

All readings taken after three weeks at 28° C. unless noted otherwise. pH of all media approximately neutral (6.8–7.2).

Color number designations taken from *Color Harmony Manual,* 1958, 4th Edition, Container Corporation of America, Chicago, Ill.

BRIEF DESCRIPTION OF THE DRAWINGS

FIG. 2 is a 300 MHz proton nuclear magnetic resonance spectrum ($D_2O$) of the Antibiotics-859A.

DETAILED DESCRIPTION

Figure 1:
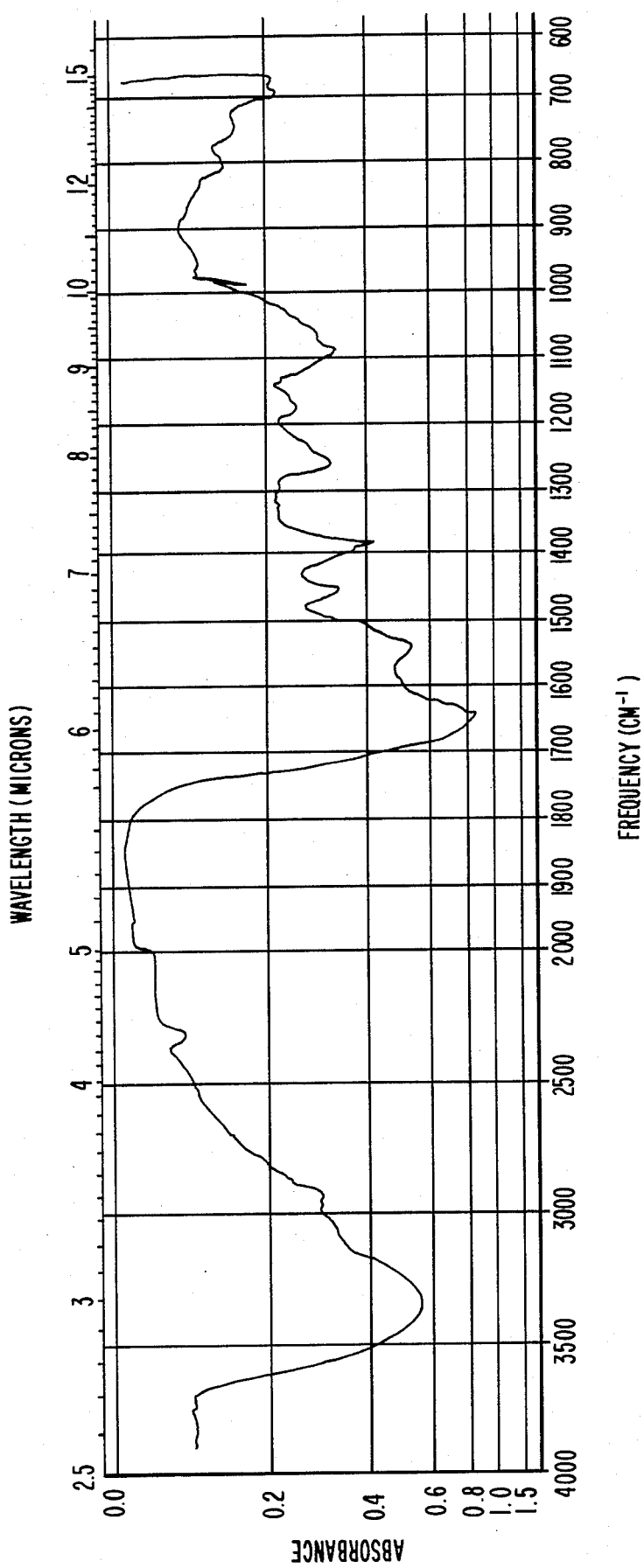
FIG. 1 is an infra red adsorption spectrum (KBr) of the Antibiotics-859A.

As used herein, the term "Antibiotics-859A" is defined to include the mixture of active antibacterial components that exhibit the chemical and physical characteristics set forth herein, produced by cultivating the *Streptomyces griseoruber* ATCC 39068 under the conditions set forth herein. As will be recognized by those artisans skilled in the fermentation arts, the number and ratio of the component antibiotics that comprise Antibiotics-859A may vary, depending upon the fermentation conditions, and the culture strain used.

It is also to be understood, that for the production of Antibiotics-859A, the present invention is not limited in its scope to the use of *Streptomyces griseoruber* ATCC 39068. It is especially desired and intended to include the use of natural and artificial mutants produced from the described organism, or other variants belonging to the genus *Streptomyces* as far as they can produce Antibiotics-859A.

In the present invention, the novel Antibiotics-859A are produced during cultivation of the microorganism, for example, *Streptomyces griseoruber* ATCC 39068, at a temperature range of from about 24° C. to 30° C., preferably 28° C. under aerobic conditions. The composition of the nutrient medium may be varied over a wide range. The essential assimilable nutrient ingredients are; a carbon source, a nitrogen source, a phosphate source and a source of inorganic elements including, sodium potassium, magnesium, sulfur, chlorine and carbonate. Cultivation is most productive under neutral to alkaline pH conditions, preferably from about 7.0 to 9.0.

Typical sources of carbon include, glucose, dextrin, starches, molasses, glycerol, and the like. Typical nitrogen sources include, vegetable meals (e.g., soy, figs, cottonseed, tomato, whole yeast preparations, corn, etc.), meat flours, various hydrolysates (casein, yeast, soybean, etc.), and amino acids.

Mineral salts such as the chlorides, nitrates, sulfates, carbonates, and phosphates of sodium, potassium, ammonium and calcium provide a source of the essential inorganic elements. The nutritive medium may also contain a number of trace elements, such as, magnesium, iron, copper, manganese, zinc and cobalt.

The maximum yield of the Antibiotics-859A can be achieved within about 72 to 168 hours, usually in about 96 hours of fermentation under optimum conditions of fermentation and aeration. The inoculum for the fermentation can be provided from suspensions, lyophylization or in combination with an inert substrate.

Following cultivation, the Antibiotics-859A may be recovered from the broth by conventional means. Generally, the basic broth (pH ca. 8.5) is acidified to about pH 6.0 with a mineral acid, for example, phosphoric acid. This acidified broth is purified by column chromatography, for example, using a non-polar adsorbent polystyrene resin such as XAD-2 resin (Rohm & Haas Co.) and eluting with an aqueous alkanol solution, for example, methanol-water (50% solution by volume or an aqueous solution of acetone (25% acetone v/v in water). The active fractions are collected and concentrated, and further purified by column chromatography, for example, using a gel filtration medium such as Sephadex LH-20 (Pharmacia Fine Chemicals, Inc.) eluting with, for example, water or a water-alkanol solution such as 10% (v/v) methanol-water mixture.

CHARACTERIZATION OF ANTIBIOTICS-859A

Purified Antibiotics-859A is a white, slightly deliquescent powder. The mixture exhibits solubility in water, but poor solubility in the lower alkanols.

Thin layer chromatography (Tlc-silica gel-E. Merck) using an elution system of methylene chloride, methanol, acetic acid and water (60:30:5:5) shows an $R_f$ of 0.50 (single spot).

The proton NMR spectrum for Antibiotics-859A is shown in FIG. 1. The characteristic data are also tabulated in Table I, below.

TABLE I

| Proton NMR Data - Antibiotics-859A | |
|---|---|
| Chemical Shift | Pattern-Coupling |
| 0.77 | d, J = 6 |
| 1.23 | d, J = 6 |
| 1.27 | d, J = 8 |
| 1.37 | d, J = 6 |
| 2.03 | (acetate) |
| 2.60 | |
| 2.67 | complex |
| 2.68 | pattern |
| 2.76 | multiplet |
| 2.88 | |
| 2.91 | |
| 2.94 | |
| 2.98 | |
| 3.09 | s |
| 4.12 | |
| 4.27 | complex pattern |
| 4.45 | multiplet |
| 4.54 | |
| 4.56 | |
| 4.18 | |
| 5.46 | d, J = 8 |
| 5.87 | d, J = 8 |
| 5.96 | |
| 6.01 | complex |
| 6.07 | pattern |
| 6.13 | multiplet |
| 6.75 | |
| 6.84 | t |
| 7.07 | d, J = 8 |
| 7.42 | d, J = 8 |
| 7.2–7.4 | complex pattern multiplet | s = singlet, d = doublet, t = triplet, J = coupling constants in Hertz (Hz) NMR solvent - $D_2O$ The spectrum from $^{252}Cf$ pulse desorption mass spectrometry showed ions up to m/e 827 $(M+Na)^+$ which corresponds to a molecular weight of 804.

The electron impact (EI) mass spectrum of the product from the treatment of the Antibiotics-859A and N,N-bis-trimethylsilyltrifluoroacetamide was obtained using an LKB-9000 mass spectrometer. The characteristic peaks are set fourth below in Table II.

TABLE II

| Electron Impact Mass Spectrum of Derivatized* Antibiotics-859A | | | |
|---|---|---|---|
| m/e | 1178 | 1106 | 1036 |
| | 999 | 927 | 955 |
| | 791 | 719 | 647 |
| | 840 | 768 | |

*Derivitized with N,N—bis-trimethylsilyl-trifluoroacetamide.

Two fractions designated were 859A1 and 859A2 eluted by reverse phase high pressure liquid chromatography, HPLC from purified cultured broth. These were each hydrolyzed overnight in constant boiling 2.5N HCl at 110°. Mass spectra (GC/MS) of the silylation products from the hydrolysis gave the major GC peaks shown in Table III. The TMS-d$_9$ peaks are not included.

TABLE III

Hydrolysis of 859A2

| Peak | Observed Mass | Comments |
|---|---|---|
| 4 | 217 | 75 + 2 TMS Gly (trace) |
| 5 | 256 | 112 + 2 TMS Uracil |
| 7 | 288 | 181 + 2 TMS p-Tyr |
| 8 | 288 | 181 + 2 TMS m-Tyr |
| 9 | 242 | 170 + 1 TMS not defined |
| 10 | 406 | 262 + 2 TMS Isomer of II |
| 11 | 406 | 262 + 2 TMS Isomer of 10 |

The second fraction, 859A1, showed similar peaks along with a small peak for possibly a third tyrosine isomer (o-Tyr). In addition, 859A1, showed a major GC peak with m/e up to 193+2 TMS and a weak peak with m/e 131+3 TMS which may be from a carbohydrate moiety.

The mass specturm of 859A2 (derivatized with TMS) itself shows peaks up to 746+6 TMS. Using a technique for poorly volatile compounds, $^{252}$Cf-PDMS (pulse desorption mass spectrometry), a presumed molecular ion of 803+Na was obtained. The mass difference m/e 57 can be ascribed to either a loss of a Gly (75-H$_2$O) or of the side chain of $CH_2CH(NHCH_3)CH(NH_2)CO_2H$ the presence of which is suspected from the NMR data.

ANTIBIOTIC ACTIVITY

Production of the Antibiotics-859A may be followed during the fermentation by testing a sample of the broth for antibiotic activity. Two useful assay organisms for testing the production are *Pseudomonas stutzeri* and *Escherichia coli*. Disk plate assays are run using ½ inch paper assay disks dipped into the supernatant of a centrifuged aliquot of the fermentation broth. The plates are incubated at 37° C. for 18–24 hours before the zones or inhibition are measured. All of the assays run on a given day were calculated from a standard curve for that day.

Antibiotic activity is generally present after 24 hours of fermentation and remains present for at least 7 days during the fermentation. Peak antibiotic production occurs at from 4 to 6 days of fermentation under optimum conditions.

The Antibiotics-859A exhibit a wide range of in vitro activity against pathogenic organisms. The in vitro activity of the Antibiotics-859A are summarized below in Table IV.

TABLE IV

In Vitro Activity of The Antibiotics-859A

| Organism | Inhibition Zone (mm) at 1 mg/ml | |
|---|---|---|
| | 859A1 | 859A2 |
| Bacillus sp. | 8 | 17 |
| Pseudomonas aeruginosa | 4 | 4 |
| Stephylococcus aureus | 0 | 7 |
| Bacillus sabtilis | 0 | 14 |
| Sarcina lutea | 22 | 25 |
| Staphylococcus aureus | 5 | 14 |
| Streptococcu faecalis | 0 | 0 |
| Salmonella gallinarum | 4 | 4 |
| Vibrio percolans | 6 | 8 |
| Proteus vulgaris | 0 | 0 |
| Escherichia coli | 9 | 31 |

TABLE IV-continued

In Vitro Activity of The Antibiotics-859A

| Organism | Inhibition Zone (mm) at 1 mg/ml | |
|---|---|---|
| | 859A1 | 859A2 |
| Pseudomonas stutzeri | 6 | 0 |
| Klebsiella pneumoniae | 6 | 7 |
| Aerobacter aerogenes | 6 | 6 |
| Pseudomonas aeruginosa | 0 | 0 |
| Escherichia coli | 0 | 4 |
| Bacillus subtilis in Chem. Defined Agr. | 0 | 15 |
| Staphylococcus aureus in Chem. Defined Agr. | 16 | 31 |
| Micrococcus flaous | 11 | 26 |
| Staphylococcus aureus | 0 | 9 |

Activities in vivo of two components are shown. These are (a) a first preparation of Antibiotics-859A tested (859A1), and (b) a sample of greater in vitro (and in vivo) activity (859A2).

Antibiotic activity in vivo is broad spectrum since there is protection against three Gram-positive organisms (*Diplococcus pneumoniae, Staphylococcus aureus,* and *Streptococcus pyogenes*) and the gram-negative *Pseudomonas aeruginosa*. Against another gram-negative organism, *Salmonella schottmuelleri* the sample of 859A2 was active to the extent of significantly prolonging the survival time of infected, treated mice.

Protection has been shown against four different strains of *Pseudomonas aeruginosa*, an organism of clinical significance. Two of the strains against which Antibiotics-859A has shown activity are clinical isolates that have multiple antibiotic resistance.

Although the majority of tests used the intraperitoneal (ip) route of therapy, activity has been also demonstrated when treatment was given subcutaneously (sc). In two tests, the sc/ip ratios were 16 and 13. Activity by the oral route was not demonstrated.

TABLE V

In Vivo Activity of Two Preparations of Antibiotics-859A Against Bacterial Infections in Mice

| Organism | Route of Therapy | ED$_{50}$ in μg × 2 dosed[a] | |
|---|---|---|---|
| | | 859A1[b] 7000 μg | 859A2[b] 163 μg |
| Diplococcus pneumoniae | ip | 10,000 | |
| Staphylococcus aureus | ip | 14,000 | 4340 |
| Streptococcus pyogenes | ip | 1,540 | 321 |
| | ip | 1,510 | 321 |
| | sc | 23,900 | 4300 |
| | po | 28,000 | 6500 |
| Proteus vulgaris | ip | 14,000 | 6500 |
| Pseudomonas aeruginosa | ip | 9,360 | 1000 |
| | ip | 9,360 | 424 |
| | ip | | 800 |
| | ip | | 200 |
| Salmonella schottmuelleri | ip | 7,000 | 6500[d] |

NOTES
[a]Infection given intraperitoneally. Therapy given by the indicated route at the time of infection and again six hours later.
[b]Potency reported as μg/ml required to give a 25 mm zone against *Pseudomonas stutzeri*, i.e., 859A1-7000; 859A2-165.
[c]Clinical isolate with multiple antibiotic resistance.
[d]No ED$_{50}$, but significant prolongation of survival time (p = 0.01) at this concentration.

859A2, carbenicillin, and gentamicin were compared in agar dilution, surface-inoculated assays at the minimum bactericidal concentration (MBC), and at ½ and ¼ of the MBC, vs four clinical isolates of Pseudomonas. Colony counts at each of the concentrations indicated that 859A-containing agar demonstrated significantly fewer colonies at ¼ and/or at ½ the MBC than did either carbenicillin or gentamicin.

Clinical isolates were supplied on nutrient agar-yeast extract slants. Strains B145 and B184 were reported as non-lactamase-containing strains whereas strains B126 and B189 contained lactamase.

A loopful of cells of each culture was transferred to 10 ml nutrient broth-yeast (NBY) extract and incubated for 16 hours at 37° C. on the shaker. The inocula were adjusted to O.D.=0.22 at 660 nm with NBY and further diluted with NBY to 1:250,000. One tenth (0.1) ml of the diluted cell suspension was added to plates containing 10 ml of Brain Heart Infusion Agar and spread uniformly over the surface with a sterile glass "hockey stick". Stock solutions of antibiotics at 10 mg/ml were added to 45° C. agar in appropriate amounts. Gentamicin and carbenicillin were manufactured by Pfizer and Schering respectively. After overnight incubation of plates at 37° C., a visual count of colonies was made.

Table VI below shows average colony counts of triplicate plates for each test. The results indicate that Antibiotics-859A2 shows equal or greater lethality over a wider concentration range than is seen with either carbenicillin or gentamicin.

TABLE VI

Comparative Lethality of 859A2, Gentamicin, and Carbenicillin vs Four Clinical Isolates of Pseudomonas in Agar Dilution Tests

| Iso-late # | 859A2 Conc. μg/ml | 859A2 # of Colonies | Carbenicillin Conc. μg/ml | Carbenicillin # of Colonies | Gentamicin Conc. μg/ml | Gentamicin # of Colonies |
|---|---|---|---|---|---|---|
| B145 | 0 | 350 | 0 | 350 | 0 | 350 |
| " | 1000 | 0 | 62.5 | 0 | 50 | 0 |
| " | 500 | 8 | 31.3 | 335 | 25 | 121 |
| " | 250 | 56 | 15.7 | 368 | 12.5 | 233 |
| B184 | 0 | 131 | 0 | 131 | 0 | 131 |
| " | 125 | 0 | 62.5 | 0 | 1.56 | 0 |
| " | 62.5 | 5 | 31.3 | 100 | 0.79 | 19 |
| " | 31.3 | 25 | 15.7 | 75 | 0.39 | 79 |
| B189 | 0 | 290 | 0 | 290 | 0 | 290 |
| " | 500 | 0 | 125 | 0 | 3.12 | 0 |
| " | 250 | 23 | 62.5 | 263 | 1.56 | 53 |
| " | 125 | 134 | 31.3 | 333 | 0.78 | 278 |
| B126 | 0 | 50 | 0 | 50 | 0 | 50 |
| " | 125 | 0 | 500 | 0 | 1.56 | 0 |
| " | 62.5 | 3 | 250 | 28 | 0.78 | 7 |
| " | 31.3 | 33 | 125 | 68 | 0.39 | 49 |

From the foregoing in vitro and in vivo data it is expected that an effective antibacterial amount of the Antibiotics-859A would be on the order of 10 mg/kg to 50 mg/kg in mammals, especially humans. The Antibiotics-859A are effective for treatment of gram negative and gram positive infections as described above, and may be administered either i.v. or s.c., alone or in combination with a pharmaceutical carrier. The ultimate choice of route and dose should be made by an attending physician and based upon the patient's unique condition.

Combinations of antibiotics with appropriate pharmaceutical carriers are accomplished by methods well known to the pharmacist's art. For purposes of subcutaneous (s.c.) administration, solutions of the antibiotic are generally employed, for example, sterile aqueous or alcoholic solutions. Such solutions should be suitably buffered if necessary and the liquid diluent may first be rendered isotonic with saline or glucose. These aqueous and alcoholic solutions are also suitable for intravenous (i.v.) injections.

The following examples illustrate the preparation and isolation of the Antibiotics-859A.

For Examples 1–9, Table VII describes the various nutrient media used. For convenience, the media will be referred to in the examples as described below.

TABLE VII

Culture Media Data

1. Lyophilized "L" Tube Preparation

The conidia and aerial mycelia from a slant culture are suspended in sterile skim milk and aliquots are transferred aseptically to small glass tubes (2 to 5 mm I.D.) which are plugged with cotton to prevent contamination. These tubes are frozen in an acetone-dry ice solution and kept cold under vacuum until the ice has sublimated. They are then sealed under vacuum and kept at 4° C. until used.

2. Seed Medium A

| | |
|---|---|
| Glucose (Reagent Grade) | 10.0 g |
| Ardamine (Autolysed yeast from Yeast Products, Inc.) | 10.0 g |
| *Phosphate buffer | 2.0 ml |
| MgSO$_4$.7H$_2$O | 0.05 gm |
| Distilled H$_2$O | 1000 ml |
| pH: adjust to 6.5 using NaOH | |
| *Phosphate Buffer | |
| Na$_2$HPO$_4$ | 95.0 g |
| KH$_2$PO$_4$ | 91.0 g |
| Distilled H$_2$O | 1000 ml |
| pH = 7.0 | |

Dispense 50 ml per 250 ml baffled Erlenmeyer flask, cotton-plug, and autoclave at 120° C. for 20 minutes.

3. Production Medium B

| | |
|---|---|
| Distillers Solubles | 20.0 g |
| Glucose | 10.0 g |
| Amber Yeast BYF 300 (Amber Labs., Inc.) | 10.0 g |
| CaCO$_3$ | 3.0 g |
| Distilled H$_2$O | 1000 ml |
| pH: adjust to 7.0 using NaOH | |

Dispense 250 ml per unbaffled Erlenmeyer flask, cotton-plug, and autoclave at 120° C. for 25 minutes.

4. Medium C

| | |
|---|---|
| Oatmeal (Gerber's Baby Food) | 20.0 g |
| Tomato Paste (Contadina) | 20.0 g |
| Add to hot Distilled H$_2$O slowly | 1000 ml |

Dispense 250 ml per unbaffled 20 L Erlenmeyer flask, cotton-plug, and autoclave at 120° C. for 25 minutes.

5. Medium D

| | |
|---|---|
| Glucose (Reagent Grade) | 10.0 g |
| Difco Asparagine | 1.0 g |
| K$_2$HPO$_4$ | 0.1 g |
| MgSO$_4$.7H$_2$O | 0.5 g |
| Difco Yeast Extract | 0.5 g |
| +Trace Element Mix #2 | 10.0 ml |
| Difco Agar | 25.0 g |
| Distilled H$_2$O | 1000 ml |
| pH: adjust to 7.2 using NaOH | |
| +Trace Element #2 | |

-continued

| | |
|---|---|
| FeSO$_4$.7H$_2$O | 1000 mg |
| MnSO$_4$.4H$_2$O | 1000 mg |
| CuCl$_2$.2H$_2$O | 25 mg |
| CaCl$_2$ | 100 mg |
| H$_3$BO$_3$ | 56 mg |
| (NH$_4$)$_6$Mo$_7$O$_{24}$.4H$_2$O | 19 mg |
| ZnSO$_4$.7H$_2$O | 200 mg |
| Distilled H$_2$O | 1000 ml |

For plates: 400 ml medium per 1 liter Erlenmeyer flask is autoclaved at 120° C. for 25 minutes and the sterilized medium transferred aseptically to sterile 15×100 mm plastic Petri plates using 20 to 25 ml/plate. The medium is allowed to solidify and the plates are stored at 4° C. until used.

For slants: The medium is transferred to 22×175 mm culture tubes using 14 ml/tube. The tubes are cotton-plugged, autoclaved at 120° C. for 15 minutes, and slanted while the medium is solidifying so as to obtain a good surface area for culture growth. The slants are then stored at 4° C. until used.

6. Medium E

| | |
|---|---|
| Amber Yeast BYF 300 (Amber Labs., Inc.) | 10.0 g |
| Distillers Solubles | 20.0 g |
| Distilled H$_2$O | 1000 ml |
| pH: adjust to 7.0 using NaOH | |

Dispense 50 ml per 250 ml baffled Erlenmeyer flask, cotton-plug, and autoclave at 120° C. for 20 minutes.

EXAMPLE 1

Pure culture ATCC 39068 was received in the "L" tube stage (see Table VII for preparation procedures). The pellet of the "L" tube was transferred aseptically to a flask of seed medium A (see Table VII for formula). This flask was shaken at 28° C. on a 220 RPM shaker (rotary motion with a 2" throw) for 2 days when good growth was obtained. A portion (1 2 ml/flask) of this broth was used to inoculate 3 second stage seed flasks (same medium and vessel as the first stage). The transfer was made aseptically using a sterile pipette. The flasks were shaken in the same manner as the first stage for 2 days. These flasks were then pooled aseptically and used to inoculate the 10 production medium flasks, aseptically, using 7 ml inoculum per flask. The production flasks contained medium B at 250 ml per 2 L unbaffled Erlenmeyer flask and were shaken at 28° C. on a 220 RPM shaker for 6 days. The assay was run on *Pseudomonas stutzeri* assay plates using ½" assay discs dipped in the supernatant of centrifuged broth. An inhibition zone of 23 mm was obtained by this procedure when the plates were incubated at 37° C. for 18-24 hours.

EXAMPLE 2

The inoculum preparation and production procedure was identical with Example 1. Only the production medium was varied. The medium for this batch was medium C (see Table VII). The 4×2 L flasks were harvested at 6 days age, pooled, assayed as in Example 1. An inhibition zone of 21 mm was obtained against *Pseudomonas stuctzeri*.

EXAMPLE 3

A mature medium D slant, inoculated using an "L" tube of culture ATCC 39068, was used to inoculate 3 medium E seed flasks (using aseptic techniques). These flasks were shaken at 28° C. for 2 days on a 220 RPM shaker. The broth from these flasks was pooled and used to inoculate 12×2 L unbaffled Erlenmeyer flasks each containing 200 ml medium B using 7 ml inoculum per flask. The production flasks were shaken at 28° C. on a 220 RPM shaker (2" throw) for 4 days at which time they were harvested. The assay, run as in example #1, gave a 32 mm inhibition zone.

Disc-plate assays were run using ½" assay discs and plates seeded with *Pseudomonas stutzeri*. The results of each experiment were calculated by assaying the starting material at several dilutions and using these results to plot a standard curve on semi-logarithmic graph paper. For simplicity, the results below are expressed in terms of units. A unit is defined as the concentration required to give a 25 mm inhibition zone in the disc-plate assay.

EXAMPLE 4

Shake flask batch from Example 1, was filtered and 1850 ml of filtrate, pH 8.1, was adsorbed on 60 ml of Dowex 1×2 chloride cycle resin. The resin was washed with water then eluted with 90% methanol/3% NH$_4$Cl, collecting 50 ml fractions. Fractions 3 through 9 were combined and concentrated to 100 ml of aqueous solution. The filtered broth assayed about 0.5 units/ml and the spent broth was inactive. The concentrated eluate assayed about 5 units/ml and the calculated yield was 55%.

EXAMPLE 5

Concentrated eluates from four shake-flask batches prepared as in Example 4 were combined to give 305 ml of concentrate. A 300 ml portion was adjusted to pH 3.0 with dilute (1N) HCl and extracted three times with 300 ml portions of n-butyl alcohol. The activity in the alcohol extracts was transferred into water by back-extracting each extract in succession with a 300 ml portion of water and adjusting the mixture to pH 7 with dilute (2.5N) NaOH each time. The water layer was concentrated to 275 ml to remove n-butyl alcohol. The yield was 50% and the product assayed about 8 units/ml. The total solids in this solution was found to be 28 mg/ml, thus the specific activity of this sample was 3.5 mg/unit, about 9x that of filtered broth.

EXAMPLE 6

The batch from Example 2, was filtered and yielded 24 liters of filtrate, pH 7.6, which assayed about 1 unit/ml. This was adsorbed on 7.5 liters of Dowex 1×2 chloride cycle resin. The adsorbate was washed with water and eluted with 30 liters of 90% methanol/3% NH$_4$Cl (v/v). The eluate was concentrated to 9.25 liters which assayed about 40 units/ml and the calculated yield was 70%.

EXAMPLE 7

A 500 ml portion of concentrate from Example 6 was diluted to 2.5 liters with water, adjusted to pH 5 with dilute (1N) HCl then adsorbed on 500 ml of Amberlite XAD-2. The adsorbate was washed with water then with 1 liter of 20% aqueous methanol (v/v). The activity was recovered by eluting with 2 liters of 50% methanol. The eluate was concentrated to 210 ml and filtered to remove some insoluble material. This concentrate, pH 4.2, contained 13.2 mg/ml of total solids and assayed 80 units/ml. The calculated yield was 60% and the specific activity was 160 μg/unit.

EXAMPLE 8

A 3.5 liter portion of concentrate from Example 6 was diluted to 17.5 liters with water, adjusted to pH 7.0 then adsorbed on 4 liters of XAD-2. The adsorbate was washed with 8 liters of water then with 8 liters of 20% aqueous methanol. The activity was recovered by eluting with 12 liters of 10% aqueous pyridine (v/v). The eluate was concentrated to one liter at pH 7.0. This concentrate contained 17.5 mg/ml of total solids and assayed 34 units/ml. The calculated yield of product 859A1 was 50% and the specific activity was 470 μg/unit. Analytical data; Found: C, 55.97; H, 5.77; N, 13.83; O (diff.), 24.47. Calculated for $C_{28}H_{34}N_6O_9$: C, 56.15; H, 5.72; N, 14.04; O, 24.05. U.V. (max) in 0.1M tris, pH 8.0; 257 nm, E (1%, 1 cm)=256.

EXAMPLE 9

The entire one liter concentrate from Example 8 was readsorbed on 600 ml of XAD-2. The adsorbate was washed with 1.2 liters of water then with 1.2 liters of 20% aqueous methanol (v/v). The water wash contained 5% and the aqueous methanol 10% of the charged bioactivity. The adsorbate was then eluted with two liters of 25% aqueous acetic acid (v/v), collecting 200 ml fractions. Fractions 1 to 5 were combined and concentrated to 25 ml. The pH of this solution was adjusted to 9.5 with concentrated ammonia and then freeze dried to yield 5.95 grams. The product 859A1 represented a 50% yield with a specific activity of 300 μg/unit.

The 20% aqueous methanol (v/v) eluant was concentrated to 50 ml. After standing at 5° C. for two days, crystals were recovered by filtration, washed with cold water and dried at 50° C., 0.1 mm pressure for 2 hour. The yield was 107 mg of 859A2 with a specific activity of 1,250 μg/unit. Analytical data; Found: C, 50.10; H, 6.34; N, 13.28; O, 30.33. Calculated for $C_{22}H_{33}N_5O_{10}$: C, 50.77; H, 6.34; N, 13.46; O, 29.43. U.V. (max) in 0.1M tris, pH 8.0; 259 nm, E (1%, 1 cm)=220.

EXAMPLE 10

A cultured broth (9 liters) was filtered using Super-Cel (0.5 liter) as a filter aid at the pH of the broth as received - about 8.5. The filtrate was adjusted to pH 6 with $H_3PO_4$. During the pH adjustment the filtrate became cloudy around pH 7 and then cleared as the pH dropped to 6. This solution was charged onto a 5×40 cm column of XAD-2, a non-polar polystyrene resin (Rohm & Haas Co.). The column was washed with a solution of 25% aqueous acetone (v/v). The activity was seen in the first two liters of eluent (Table VIII). Fractions 2 to 6 (1.2 l) were combined and concentrated in vacuo to 100 ml for the next step.

The concentrated solution from the XAD-2 resin was charged onto a 5×120 cm column of Sephadex LH-20, a gel filtration resin (Pharmacia Fine Chemicals, Inc.) and was eluted with a solution of 10% aqueous methanol (v/v). The active components were eluted as a main peak. Component 859A1 was eluted in two void volumes and the second fraction, component 859A2 was obtained as a weak peak at three void volumes of the eluting solvent.

TABLE VIII

Antibody Activity of the XAD-2 Eluent From Example 10

| Fraction[a] (200 ml each) | E. coli | Zone Diameter[b] P. Aeruginosa |
|---|---|---|
| 1 | — | — |
| 2 | 17 | 22 |
| 3 | 23 | 27 |
| 4 | 20 | 24 |
| 5 | 16 | 23 |
| 6 | 15 | 21 |
| 7 | 9 | 16 |
| 8 | 7 | 15 |
| 9 | — | — |
| 10 | — | — |
| 11 | — | — |

[a]The fractions were collected shortly after start of the 25% acetone solvent. A brown color developed part way through the elution of the fraction (void volume).
[b]The assays were made by dipping ¼" discs into the fractions. The discs were vacuum dried before being placed on the agar plates. Zone of growth inhibition diameters are shown in mm.

Claims of the invention to follow.
What is claimed is:

1. The Antibiotics-859A, produced by the controlled aerobic fermentation of *Streptomyces griseoruber* ATCC 39068 in an aqueous nutrient medium at a temperature range of 20° to 30° C., a pH range of 7.0 to 9.0 and a time range of from 24 to 200 hours, which has the following characteristics in its essentially pure form:
   (a) white, slightly deliquescent powder.
   (b) soluble in water,
   (c) insoluble in lower alkanols,
   (d) tlc ($CH_2Cl_2$/MeOH/AcOH/$H_2O$ 60:30:5:5) $R_f$=0.50
   (e) $UV\lambda_{Max}^{H_2O} 258$, E%=208
   (f) Characteristic IR (Kbr) as shown in FIG. 1,
   (g) Characteristic proton NMR ($D_2O$) as shown in FIG. 2 with data as follows: Peaks at $\delta$=0.77 (d, J=6), 1.23 (d, J=6), 1.27 (d, J=8), 1.37 (d, J=6), 2.03 (acetate), a complex pattern including peaks at=2.60, 2.67, 2.68, 2.76, 2.88, 2.91, 2.94 and 2.98, 3.09 (s), a group including multiplets centered at=4.12, 4.27, 4.45, 4.54, 4.56 and 4.18, 1.81 (HOD peak), 5.46 (d, J=8), 5.87 (d, J=8), and a pattern including peaks at 5.96, 6.01, 6.07, 6.13 and 6.75, 6.84 (t), 7.07 (d, J=8), 7.42 (d, J=8) and a complex pattern at=7.2–7.4 (chemical shifts $\delta$ in ppm, coupling constants J in Hertz (Hz),
   (h) the spectrum from $^{252}Cf$ pulse desportion mass spectrometry shows ions up to m/e 827 (M+Na)+ which corresponds to a M.W. of 804,
   (i) the electron impact mass spectrum of the product from treatment of the antibiotic with N,N-bis-trimethylsilyltrifluoroacetamide shows characteristic peaks in the high mass region at m/c 1178, 1106, 1036, (746+4 to 6 ($C_3H_8Si$)); 999, 927, 955, (639+3 to 5 ($C_3H_8Si$)); 791, 719, 647 (431+2 to 4 ($C_3H_8Si$)); 840, 768 (522+3 to 4 ($C_3H_8Si$)),
   (j) derivatization products from acid hydrolysis of the Antibiotics-859A give mass spectral evidence for the presence of uracil, tyrosine, phenylalanine, alanine and α, β-diaminobutyric acid.

2. The process for producing the Antibiotics-859A of claim 1 which comprises cultivating an Antibiotics-859A producing strain of *Streptomyces griseoruber* ATCC 39068 under controlled aerobic conditions in an aqueous nutrient medium "until substantial antibiotic activity is imparted to said medium".

3. The process of claim 2 for producing and accumulating the Antibiotics-859A which further comprises cultivating the *Streptomyces griseoruber* ATCC 39068 under controlled aerobic conditions in an aqueous nutrient medium at a temperature range of from about 24° C. to 30° C. for at least 24 hours, and a pH range of 7.0 to 9.0.

4. The process of claim 3 which further comprises isolating the accumulated Antibiotics-859A from the cultured broth.

5. The process of claim 3 wherein the isolation of Antibiotics-859A is accomplished by:
 (a) filtering the cultured broth;
 (b) adjusting the filtrate pH to 6.0 with a mineral acid;
 (c) purifying the adjusted filtrate by chromatographic means.

6. The process of claim 5 wherein said chromatographic means comprise:
 (a) Eluting the filtrate on a non-polar polystyrene adsorbant resin, eluting with, first, water and second, a mixture of 25% aqueous acetone (v/v), followed by concentration in vacuo and,
 (b) charging the concentrate from (a) onto a suitable gel filtration medium and eluting with 10% aqueus methanol (v/v).

7. An injectable pharmaceutical composition for inhibiting the growth of gram negative and gram positive microorganisms, said composition comprising a therapeutically effective amount of the Antibiotics-859A as defined in claim 1 and a pharmaceutical carrier.

8. A method of treating gram negative or gram positive infections in mammals which comprises intravenously or subcutaneously administering a therapeutically effective amount of the Antibiotics-859A as defined in claim 1 in a pharmaceutical carrier.

* * * * *